US006653466B2

(12) United States Patent
Matsuo

(10) Patent No.: US 6,653,466 B2
(45) Date of Patent: Nov. 25, 2003

(54) PHARMACEUTICAL COMPOSITION FOR TREATMENT OF DUCHENNE MUSCULAR DYSTROPHY

(75) Inventor: Masafumi Matsuo, 3-31 Kitaochiai 5-chome, Suma-ku, Kobe-shi, Hyogo 654-0151 (JP)

(73) Assignees: JCR Pharmaceuticals Co., Ltd., Hyogo (JP); Masafumi Matsuo, Hyogo (JP)

( * ) Notice: Subject to any disclaimer, the term of this patent is extended or adjusted under 35 U.S.C. 154(b) by 0 days.

(21) Appl. No.: 09/917,907

(22) Filed: Jul. 31, 2001

(65) Prior Publication Data

US 2001/0056077 A1 Dec. 27, 2001

Related U.S. Application Data

(63) Continuation of application No. 09/563,260, filed on May 1, 2000, now abandoned.

(30) Foreign Application Priority Data

May 21, 1999 (JP) ............................................. 11-140930

(51) Int. Cl.$^7$ ............................ C07H 21/04; C12Q 1/68; C12P 19/34

(52) U.S. Cl. ................ 536/24.3; 536/24.31; 536/24.33; 536/24.5; 435/6; 435/91.1

(58) Field of Search ............................ 435/6, 91.1, 325, 435/375; 536/24.3, 24.31, 24.33, 24.5; 514/44

(56) References Cited

U.S. PATENT DOCUMENTS

| | | | |
|---|---|---|---|
| 5,151,510 A | 9/1992 | Stec et al. | |
| 5,151,520 A | 9/1992 | Gottschalk et al. | |
| 5,627,274 A | 5/1997 | Kole et al. | |
| 5,665,593 A | 9/1997 | Kole et al. | |
| 5,916,808 A | 6/1999 | Kole et al. | |
| 5,948,680 A | 9/1999 | Baker et al. | |
| 5,976,879 A | 11/1999 | Kole et al. | |

FOREIGN PATENT DOCUMENTS

| | | |
|---|---|---|
| EP | 1 054 058 A1 * | 5/2000 |
| EP | 1054058 | 11/2000 |
| JP | 2000-125448 | 4/2000 |
| JP | 2000-348957 | 12/2000 |
| WO | 89/06286 | 7/1989 |
| WO | 94/26887 | 11/1994 |

OTHER PUBLICATIONS

K–Y Jen et al., Stem Cells, "Suppression of Gene Expression by Targeted Disruption of Messenger RNA: Available Options and Current Strategies," 2000, 18:307–319.*

DW Gene et al.,American College of Surgeons, "Antisense Oligonucleotides: An Evolving Technology for the Modulation of Gene Expression in Human Disease," Jul. 2000,vol. 191, No. 1, pp. .93–105.*

AD Branch, TIBS, "A good antisense molecule is hard to find," Feb. 1998, pp. 45–50.*

S Agrawal et al., Molecular Medicine Today,"Antisense therapeutics: is it as simple as complementary bass recognition?" Feb. 2000, vol. 6, pp. 72–81.*

JCT van Deutekom et al., Human Molecular Genetics, "Antisense–induced exon skipping restores dystrophin expression in DMD pateint derived muscle cells,"2001, vol. 10, No. 15, pp. 1547–1554.*

Ito et al., *Amer. J. Human Genetics*, vol. 65(4), pp. A188 (1999).

English Language Abstract of JP 2000–125448.

English Language Abstract of JP 2000–348957.

Askari et al., "Molecular Medicine Antisense–Oligonucleotide Therapy", N. Engl. J. Med., vol. 334, pp 316 to 318 (1996).

Trojan et al., "Treatment and Prevention of Rat Glioblastoma by Immunogenic C6 Cells Expressing Antisense Insulin–Like Growth Factor I RNA", Science, vol. 259, pp 94 to 97 (1993).

Trojan et al., "Loss of Tumorigenicity of Rat Glioblastoma Directed by Episome–Based Antisense cDNA Transcription of Insulin–Like Growth Factor I", Proc. Nat.. Acad. Sci. USA, vol. 89, pp 4874–4878 (1992).

Koenig et al., "Complete Cloning of the Duchenne Muscular Dystrophy (DMD) cDNA and Preliminary Genomic Organization of the DMD Gene in Normal and Affected Individuals", Cell, vol. 50, pp 509–517 (1987).

Nishio et al., "Identification of a Novel First Exon in the Human Dystrophin Gene and of a New Promoter Located More Than 500 kb Upstream of the Nearest Known Promoter", J. Cllin. Invest., vol. 94, pp 1037–1042 (1994).

Roberts et al., "Exon Structure of the Human Dystrophin Gene", Genomics, vol. 16, pp 536–538 (1993).

Ahn et al., "The Structural and Functional Diversity of Dystrophin", Nature Genet., vol. 3, pp 283–291 (1993).

D'Souza et al., "A Novel Dystrophin Isoform is Required for Normal Retinal Electrophysiology", Hum. Mol. Genet., Vol 4, pp 837 to 842 (1995).

Hoffman et al., "Dystrophin Abnormalities in Duchenne/Becker Muscular Dystrophy", Neuron, vol. 2, pp 1019 to 1029 (1989).

(List continued on next page.)

Primary Examiner—Karen Lacourciere
(74) Attorney, Agent, or Firm—Greenblum & Bernstein P.L.C.

(57) ABSTRACT

A therapeutic pharmaceutical composition for patients of Duchenne muscular dystrophy with entire loss of exon 20 in dystrophin mature mRNA is provided. The composition comprise as an active principle an antisense oligonucleotide consisting of a 20 to 50-nucleotide sequence against exon 19 of the dystrophin pre-mRNA.

16 Claims, No Drawings

OTHER PUBLICATIONS

Chamberlain et al., "Deletion Screening of the Duchenne Muscular Dystrophy Locus via Multiplex DNA Amplification", Nucleic Acids Res., vol. 16, pp 11141 to 11156 (1988).

Beggs et al., "Detection of 98% of DMD/BMD Gene Deletions by Polymerase Chain Reaction", Hum. Genet., vol. 86, pp 45 to 48 (1990).

Monaco et al., "An Explanation for the Phenotypic Differences between Patients Bearing Partial Deletions of the DMD Locus", Genomics, vol. 2, pp 90 to 95 (1988).

Sakuraba et al., "Invariant Exon Skipping in the Human $\alpha$–Galactosidase A Pre–mRNA: A $g^{+1}$ to t Substitution in a 5'–Splice Site Causing Fabry Disease", Genomics, vol. 12, pp 643 to 650 (1992).

Matsuo et al., "A Very Small Frame–Shifting Deletion Within Exon 19 of the Duchenne Muscular Dystrophy Gene", Biochem. Biophys. Res. Commun., vol. 170, pp 963 to 967 (1990).

Matsuo et al., "Exon Skipping during Splicing of Dystrophin mRNA Precursor due to an Intraexon Deletion in the Dystrophin Gene of Duchenne Muscular Dystrophy Kobe", J. Clin. Invest., vol. 87, pp 2127 to 2131 (1991).

Hagiwara et al., "A Novel Point Mutation ($G^{-1}$ to T) in a 5' Splice Donor Site of Intron 13 of the Dystrophin Gene Results in Exon Skipping and Is Responsible for Becker Muscular Dystophy", Am. J. Hum. Genet., vol. 54, pp 53 to 61 (1994).

Matsuo et al., "Partial Deletion of a Dystrophin Gene Leads to Exon Skipping and to Loss of an Intra–Exon Hairpin Structure From the Predicted mRNA Precursor", Biochem. Biophys. Res. Commun., vol. 182, pp 495 to 500 (1992).

Dietz et al., "The Skipping of Constitutive Exons in Vivo Induced by Nonsense Mutations", Science, vol. 259, pp 680 to 683 (1993).

Takeshima et al., "Modulation of In Vitro Splicing of the Upstream Intron by the Modifying an Intra–Exon Sequence Which is Deleted from the Dystrophin Gene in Dystrophin Kobe", J. Clin. Invest., vol. 95, pp 515 to 520 (1995).

Watakabe et al., "The Role of Exon Sequences in Splice Site Selection", Genes Dev., vol. 7, pp 407 to 418 (1993).

Pramono et al., "Induction of Exon Skipping of the Dystrophin Transcript in Lymphoblastoid Cells by Transfecting an Antisense Oligodeoxynucleotide Complementary to an Exon Recognition Sequence",Biochem. Biophys. Res. Commun., vol. 226, pp 445 to 449 (1996).

Zon et al., "Phosphorothioate Oligonucleotides", in Oligonucleotides and Analogues A Practical Approach (F. Eckstein, ed.,) pp 87 to 108 (Oxford University Press, Oxford, England), 1998.

Martin, "Early Clinical Trials with GEM 91, A Systemic Oligodeoxynucleotide", *Applied Antisense Oligonucleotide Technology*, pp. 387–393 (1998).

Dunckley et al., "Modification of Splicing in the Dystrophin Gene in Cultured Mdx Muscle Cells by Antisense Oligoribonucleotides", *Human Molecular Genetics*, vol. 5, No. 1, pp. 1083–1090 (1995).

Bulfield et al., "X Chromosome–Linked Muscular Dystrophy (mdx) in the Mouse", *Proc. Natl. Acad. Sci.*, 81:1189–1192 (1984).

Morgan, "Cell and Gene Therapy in Duchenne Muscular Dystrophy", *Human Gene Ther.*, 5:165–173 (1994).

Nicholson et al., "Dystrophin in Skeletal Muscle",*J. Neurol. Sci.*, 94:137–146 (1989).

Klein et al., "Somatic Reversion/Suppression in Duchenne Muscular Dystrophy (DMD): Evidence Supporting a Frame–Restoring Mechanism in Rare Dystrophin–Positive Fibers", *Am. J. Human Genetics*, 50:950–959 (1992).

Wilton et al., "Dystrophin Gene Transcripts Skipping the mdx Mutation", *Muscle & Nerve*, 20:728–734 (1997).

Inoue et al., "Binding of the Drosophila Transformer and Transformer–2 Proteins to the Regulatory Elements of Doublesex Primary Transcript for Sex–Specific RNA Processing", *Proc. Natl. Acad. Sci.*, 89:8092–8096 (1992).

Crooke, Antisense Research and Application, Springer, New York, pp. 1–50, 1998.

Agrawal, "Antisense Oligonucleotides: towards clinical trials", TIBtech, vol. 14, pp. 376–387, 1996.

* cited by examiner

SEQUENCE LISTING

<160> NUMBER OF SEQ ID NOS: 2

<210> SEQ ID NO 1
<211> LENGTH: 16
<212> TYPE: DNA
<213> ORGANISM: Homo sapiens

<400> SEQUENCE: 1
gcaagatgcc agcaga

-continued

```
<210> SEQ ID NO 2
<211> LENGTH: 31
<212> TYPE: DNA
<213> ORGANISM: Homo sapiens

<400> SEQUENCE: 2
aactgcaaga tgccagcaga tcagctcagg c                              31
```

PHARMACEUTICAL COMPOSITION FOR TREATMENT OF DUCHENNE MUSCULAR DYSTROPHY

CROSS-REFERENCE TO RELATED APPLICATION

This application is a continuation application of U.S. application Ser. No. 09/563,260 filed May 1, 2000, now abandoned, and which claims priority of Japanese Application No. 140930/99, filed May 21, 1999. The entire disclosure of U.S. application Ser. No. 09/563,260 is considered as being part of the disclosure of this application, and the entire disclosure of U.S. application Ser. No. 09/563,260 is expressly incorporated by reference herein in its entirety.

FIELD OF THE INVENTION

The present invention relates to the use of an antisense oligonucleotide for the manufacture of a therapeutic pharmaceutical composition for a certain hereditary disease, and more specifically to a therapeutic pharmaceutical composition for Duchenne muscular dystrophy intended to induce an exon skipping in the pre-mRNA of a certain abnormal dystrophin gene.

BACKGROUND OF THE INVENTION

Antisense oligonucleotide strategy has been widely studied for the purpose of inhibiting expression of oncogenes or viral genes. Antisense oligonucleotides have been known to efficiently inhibit de novo synthesis of their respective targeted proteins. For example, it is known that an antisense oligonucleotide against the mRNA encoding IGF-I (Insulin-like Growth Factor-I) inhibits proliferation of rat glioblastoma cells [Askari, F. K., and McDonnell, W. M., N. Engl. J. Med, 334: 316–318 (1996); Trojan, et al., Science, 259: 94–97 (1993), Trojan, et al., Proc. Natl Acad. Sci. U.S.A., 89: 4874–4878 (1992)].

In addition, a method has been reported to inhibit an abnormal splicing of a pre-mRNA by means of its antisense oligonucleotide [Japanese Laid-Open Patent Publication No. H08-510130].

Today, diagnosis has become available for some hereditary diseases caused by abnormal splicing of the corresponding pre-mRNA, and an intractable disease, muscular dystrophy, has come to draw particular attention. Muscular dystrophy is grossly classified into Duchenne muscular dystrophy (DMD) and Becker muscular dystrophy (BMD). DMD is a hereditary muscular disease of highest incidence, occurring in one out of 3,500 newborn boys. Patients of DMD exhibit lowered muscular power in their infancy at first, and, after suffering from consistent muscular atrophy from then on, eventually die at the age of about 20. At present, no effective therapeutic drug is available for DMD, and therefore development of such a therapeutic has been longed for by patients all over the world. In 1987, dystrophin gene as the causative gene of DMD was found with the aid of retrospective genetics, and BMD also was found to occur from abnormality of the same dystrophin gene [Koenig, M. et al., Cell, 50:509–517(1987)]. As for BMD, its onset is relatively late, which is noted in the adulthood, and, though a mild loss of muscular power is observed after the onset of the disease, nearly normal life is allowed.

Dystrophin gene is located in the subregion 21 of the short arm or the X-chromosome. Nishio et al. revealed the size of dystrophin gene to be 3,000 kb, which is the largest known human gene [Nishio, H. et al., J. Clin. Invest., 94:1037–1042 (1994)]. Despite that large size, regions of only 14 kb in total of the dystrophin gene encode dystrophin protein, and the encoding regions are divided into 79 exons distributed within the gene [Roberts, R G., et al., Genomics, 16:536–538(1993)]. Furthermore, the gene includes seven distinct promoter regions, which are also distributed within the gene and responsible for production of respective distinct mRNAs [Nishio, H., et al., J. Clin. Invest., 94:1073–1042(1994), Ann, A H. and Kunkel, L M., Nature Genet., 3:283–291(1993), D'Souza, V N. et al., Hum. Mol. Genet., 4:837–842(1995)]. Thus, there is high structural complexity resides in dystrophin gene and its transcript.

Genetic diagnosis of DMD and BMD was performed in early days using fragments of dystrophin gene, and then by Southern blot analysis with cDNA probes. It thereby was revealed that about six tenth of DMD/BMD patients have abnormalities of large loss or multiplication in dystrophin gene [Hoffman, E P. and Kunkel, L M., Neuron, 2:1019–1029(1989)]. Most of the abnormalities found in the gene in DMD/BMD patients is a loss occurring in the gene, with sizes of as big as several kb. For genetic diagnosis, as the abnormalities are concentrated on two hot-spots in dystrophin gene, multiplex PCR was designed, which can conveniently identify a deletion using two PCR (polymerase chain reaction) systems focusing on 19 exons in those hot-spots [Chamberlain J S., et al., Nucleic Acids Res., 16:11141–11156(1988), Beggs A H., et al., Hum. Genet., 86:45–48(1990)]. Today, the multiplex PCR has become the most popular diagnosing method, for it quickly gives results and can detect 98% of gene abnormalities detectable by Southern blotting.

No explanation was given to the cause of the big difference in pathological conditions clinically observed between the two diseases, DMD and BMD, resulting from apparently similar abnormalities in the same dystrophin gene until so-called frameshift hypothesis was proposed [Monaco, A P., et al., Genomics, 2:90–95(1988)]: In DMD, a partial deletion present in the gene results in a (out-of-frame) shift of amino acids reading frame along the dystrophin mRNA and an eventually emerging stop codon puts an end to the dystrophin synthesis halfway. In contrast, in BMD, the reading frame is kept intact (in-frame) in spite of a partial deletion present in the gene and dystrophin protein therefore is synthesized, though different in size from wild dystrophin. In fact, analyses of dystrophin in patients' muscle demonstrated that dystrophin is lost in DMD, whereas it occurs in BMD, with an altered staining property, though. In addition, the according to comparisons made of the phenotypes, DMD and BMD, with the types of reading frames deduced from the abnormalities in dystrophin gene, frameshift hypothesis has been found proper in more than 90% of the patients.

Genetic information transcribed from the gene undergoes splicing to remove introns and thus mature mRNA is produced, which exclusively consists of exons. The mature mRNA is then translated in accordance with its reading frame to synthesize a protein strictly in consistent with the genetic information encoded in the gene. In the splicing step of pre-mRNA, there is a mechanism for precisely distinguishing introns from exons in the nucleotide sequence of the pre-mRNA. For this purpose, sequences in intron-exon boundaries are conserved in every gene in certain rules, and thus known as consensus sequences.

Consensus sequences are known at three sites: a splice donor site at the 5' end of an intron (the site providing an exon-intron junction), a splice acceptor site at the 3' end of the intron, and a branch site.

It has been reported concerning a number of diseases that substitution of just a single nucleotide in one of these consensus sequences results in abnormal splicing, indicating that the consensus sequences are the keys to splicing [Sakuraba, H. et al., Genomics, 12: 643–650 (1992)].

Upon this background, the present inventors investigated for the purpose of providing a pharmaceutical agent to correct the expression of abnormal genes through artificial regulation of pre-mRNA splicing.

The present inventors for the first time in Japan performed a PCR diagnosis of dystrophin gene abnormalities for DMD/BMD patients, and thereby revealed that there is no significant difference between westerners and Japanese in the type of abnormalities in the gene, i.e., no significant difference exists among these races. Though the gene abnormalities thus found by the genetic diagnosis were, without exception, gigantic ones involving several kb to several hundred kb nucleotides, further analyses for the first time led to successful identification of the nucleotide sequence of the deleted part of a dystrophin gene, and the result was reported along with the corresponding case named "dystrophin Kobe" [Matsuo, M, et al., Biochem. Biophys. Res. Commun., 170:963–967(1990)].

The one with the gene abnormality named "dystrophin Kobe" is a DMD case. The results of its multiplex PCR analyses revealed that no band of amplified genomic DNA corresponding to exon 19 was found at its expected position, apparently indicating loss of exon 19. However, after a reaction attempted to amplify the exon 19 region of the genomic DNA, exon 19, though smaller than its normal size, was detected as the amplification product, indicating that the disease was not brought about a simple exon deletion frequently observed in dystrophin gene. PCR amplification was performed on dystrophin exon 19 region from the family members of the patient. With the DNAs from his mother and younger sister, it gave, along with normal one, an amplification product of the same size as the patient's product, indicating that the former two were carriers of this abnormal gene.

Then sequencing of the abnormal product of the amplification obtained from the patient showed that 52 nucleotides were lost from exon 19, which is made up of 88 nucleotides. The loss of these 52 nucleotides from the exon sequence implies that a shift of the reading frame is resulted in the dystrophin mRNA (rendering it out-of-frame) and thus giving rise to a stop codon within exon 20. The result of the genetic diagnosis was consistent with the clinically given diagnosis of DMD.

To examine the effect of the lost part of exon 19 identified in dystrophin Kobe on splicing, dystrophin mRNA from the patient was analyzed [Matsuo, M., et al., J. Clin. Invest., 87:2127–2131(1991)].

First, using mRNA from leukocytes of the patient and reverse transcriptase, cDNA was prepared, which then was amplified by nested-PCR. Amplification of a region covering from exon 18 through exon 20 gave an amplified fragment, which was smaller than the size expected from the identified abnormality in the genome. This suggested a possibility that the mRNA had another abnormality different from the one in genomic DNA or that there existed some difference between the mRNAs from leukocytes and the muscular cells. Then, in order to make sure that this mRNA abnormality is shared also by the mRNA from muscular cells, which are associated with the disease, cDNA prepared from mRNA from muscular cells was used as a template in PCR to amplify a region covering from exon 18 through exon 20. The product thus obtained was the same as the amplification product of the region covering exon 18 through exon 20 from leukocytes.

Then, sequencing of the thus obtained small-sized abnormal amplification product revealed that entire exon 19 sequence was lost from dystrophin cDNA of the dystrophin Kobe patient, with exon 18 directly connected to exon 20. This result was not in agreement with the fact that the genomic exon 19 sequence lacked just 52 nucleotides, with the other 36 nucleotides remaining in place. This indicates that in dystrophin Kobe, an exon skipping took place in the maturation process of pre-mRNA by splicing out of the remaining 36 nucleotides in exon 19.

A number of cases have been reported in which exon skipping occurs as a result of abnormality of a gene. It was reported for the first time by the present inventors that a point mutation in dystrophin gene caused an exon skipping [Hagiwara, Y., Am. J. Hum. Genet., 54:53–61(1994)]. All of these mutations of the gene causing exon skipping were those localized in consensus sequences, which determine the splicing sites as aforementioned.

In contrast, in dystrophin Kobe found by the present inventors, no abnormality was detected in consensus sequences, with 52 nucleotides found deleted just from "thin" the exon. The reason of the exon skipping in the case, therefore, was unknown.

As the exon skipping found in dystrophin Kobe was not attributable to an abnormality in the primary structure of its DNA or pre-mRNA, the cause of the exon slipping was expected to reside in an abnormality in the secondary structure of its pre-mRNA. Thus, its secondary structure was analyzed. Analysis was done on computer using an algorithm by Zuker et al. designed for calculation of the secondary structure with the most energetically stable bonding of bases [Matsuo, M. et al., Biochem. Biophys. Res. Commun., 182:495–500(1992)]. According to an analysis of the 617 bases including nucleotide sequences of wild-type dystrophin exon 19 and the introns on both sides, the pre-mRNA was shown to have a relatively simple stem-loop structure. A characteristic intra-exon hairpin structure was noted, in which base pairs were made within the exon 19 sequence itself. In contrast, deduction from the sequence of the exon with the 52-base intra-exon deletion of dystrophin Kobe and the adjacent introns gave a result greatly different from that of the wild type. The most notable feature of dystrophin Kobe was that it had a simple stem structure in which the exon sequence makes pairs only with an intron sequence. This result suggested that the intra-exon hairpin structure found in the wild type might be the factor characteristic of the exon structure of dystrophin gene.

Then, 22 exons for which the sequence of the adjacent introns were known were chosen from the 79 exons of dystrophin gene, and the secondary structures of their pre-mRNA were analyzed. The results showed that all the exons analyzed had an intra-exon hairpin structure. Thus, the presence of an intra-exon hairpin structure was thought to be an essential element for a exon to function. These findings strongly suggested that the exon skipping found in dystrophin Kobe occurred due to the elimination of the intra-exon hairpin structure in its pre-mRNA. Also suggested was that some exon sequence itself played an important role in the recognition of exon during splicing.

Recently, it was reported that, in addition to an abnormality in the consensus sequences, an abnormal sequence within an exon could also cause exon skipping [Dietz, H C., et al., Science, 259:680–683(1993)]. Thus, attention has been drawn not only to the consensus sequences but also to exon sequences as factors serving to decide splicing sites. These have thrown over the conventional concept of splicing in molecular biology.

As it was suggested that a sequence within exon 19 would be important in determining the splicing site, an in vitro splicing system was constructed and a test carried out to demonstrate it [Takeshima, Y., et al., J. Clin. Invest., 95:515–520(1995)]. First, a mini-gene was created consisting of exons 18 and 19 plus intron 18 of dystrophin gene. A radioisotope-labelled pre-mRNA was synthesized from the mini-gene. The pre-mRNA thus obtained was mixed with Hela cell nucleus extract and splicing was allowed to proceed in vitro. Thus produced mature mRNA was separated by electrophoresis. In this reaction system, splicing occurred as normal with pre-mRNA having normal exon 19, giving a mature mRNA which had directly connected exons 18 and 19. When the exon 19 sequence was replaced with that of dystrophin, however, the mature mRNA was not obtained. This indicated that the 52 nucleotide lost from exon 19 in dystrophin Kobe had an important role in splicing.

This abnormal splicing, however, might have been due to the "size" of exon 19 which was shortened to 36 nucleotides. Thus, an experiment was carried out in similar manner after insertion of the deleted sequence of exon 19 of dystrophin Kobe in the opposite orientation for making up for the loss. With this pre-mRNA, splicing took place but only with a low efficiency. This result indicated that splicing efficiency is lowered with an abnormal intra-exon sequence even when the exon is of a normal length, and further indicated that it is the nucleotide sequence of the exon (not its size) that is important.

Then, in order to examine the effect of intra-exon nucleotide sequences on splicing, pre-mRNAs were synthesized containing one of two different sequences inserted for the lost 52 nucleotides and their efficiency of splicing was examined. With two pre-mRNAs containing an inserted fragment of β-globin gene or ampicillin resistance gene, splicing was observed but with a very low efficiency. However, the β-globin gene insertion resulted in relatively high splicing efficiency compared with the insertion of the ampicillin resistance gene. The former nucleotide sequence is rich in purine bases and a purine-dominated sequence within an exon is thought to take part in exon recognition [Watanabe, A., et al., Genes Dev., 7:407–418(1993)].

These results of experiments demonstrated that not only a consensus sequence but also a sequence within the downstream exon is involved in splicing, introducing new concept into processing of genetic information.

Regulation of Splicing with Antisense Oligonucleotide

Based on the above finding that a sequence within exon 19 of dystrophin gene is highly-important for its splicing to take place, the inventors continued the study focusing on the possibility that abnormal splicing could be induced artificially by breaking the sequence and.

Thus, an 2'-O-methyl oligoRNA was synthesized which is complementary to the 31-nucleotide sequence set forth under SEQ ID NO:2 in the Sequence Listing that contains the nucleotide sequence set forth under SEQ ID NO:1 in the Sequence Listing, which is part of the 52-nucleotide sequence lost in dystrophin Kobe. Using the aforementioned in vitro splicing system, assessment was made on the effect of the oligoRNA on splicing of pre-mRNA consisting of exon 18-intron 18-exon 19. The results showed an inhibition of the splicing reaction, which was dependent on the amount of added antisense oligonucleotide and the duration of reaction. Thus, it was for the first time proved experimentally that splicing of an exon of dystrophin can be inhibited by an antisense oligonucleotide. This then suggested that splicing reaction occurring in the nucleus could be artificially manipulated [Takeshima, Y. et al., J. Clin. Invest., 95:515–520(1995)].

Regulation of Splicing within the Nucleus

To examine whether it is also possible with the antisense oligonucleotide to regulate splicing of dystrophin pre-mRNA within the nucleus of living cells, the present inventors introduced into human normal lymphoblastoid cells an antisense oligoDNA having a nucleotide sequence complementary to the nucleotide sequence set forth under SEQ ID NO:2 in the Sequence Listing that contained the nucleotide sequence set forth under SEQ ID NO:1, and then analyzed the dystrophin mature mRNA thus produced in the presence of the antisense oligoDNA [Zacharias A. D P. et al., B.B.R.C., 226:445–449(1996)]. Briefly, introduction of the antisense oligoDNA into the nucleus was conducted by mixing it with LipofectAMINE and adding the mixture to the culture medium of the lymphoblastoid cells. As a result it was found that, despite the previous results obtained with the in vitro splicing system, skipping of exon 19 was induced in the human lymphoblastoid cells by the antisense oligoDNA against the nucleotide sequence of dystrophin exon 19, thus giving rise to a mRNA in which exon 18 is connected directly to exon 20. Extended duration of culture led to a complete induction of this exon skipping, thus exclusively providing a mRNA from which exon 19 was deleted. It was further confirmed that splicing process with regard to the other exons was not affected by the antisense oligoDNA.

Therapeutic Application of Artificially Induced Exon Skipping

As noted above, DMD consists in an abnormality which shifts the amino acids reading frame of dystrophin mRNA, rendering it out-of-frame. Should this abnormal reading frame be changed to an in-frame arrangement, then DMD would be converted to BMD, and therefore amelioration of the symptoms would be expected. Assuming a patient with a simple loss of exon 20, for example, his phenotype will be of DMD, for the simple loss of exon 20, which consists of 242 nucleotides, naturally causes a frameshift and thereby allowing a stop codon to emerge halfway in the process of translation, thus leading to the cessation of dystrophin synthesis halfway. However, if exon 19 skipping could be artificially induced by administering to the patient an antisense oligonucleotide against exon 19, such as the one used in the aforementioned experiment, the reading frame could be made to turn in-frame, since total 330 nucleotides would be lost from the pre-mRNA because of the loss of 242 nucleotides of exon 20 plus 88 nucleotides of exon 19. Therefore, DMD could be converted to BMD, at least theoretically.

As mentioned above, however, dystrophin gene is very complex in structure and its pre-mRNA also takes a complex secondary structure containing a number of large introns to be spliced out, which structure regulates the normal procession of splicing. Therefore, such practical applicability was unpredictable as; whether skipping of exon 19 could be induced not only in normal human lymphoblastoid cells but also in myoblasts from a patient with simple exon 20 deletion as desired by an antisense oligonucleotide against exon 19; whether, assuming that exon 19 skipping successfully was induced, a shift of the mRNA reading frame, from out-of-frame to in-frame position, could take place without affecting the splicing-out of exon 20 or splicing at other sites in that pre-mRNA already having an abnormality causing splicing out of exon 20; or whether, assuming the in-frame conversion was achieved, thus produced mRNA could serve to efficiently produce a dystrophin-like protein.

Upon this background, the objectives of the present invention are to determine whether an antisense oligonucleotide against exon 19 can induce splicing out of the exon in cells from a DMD patient with entire loss of exon 20 in dystrophin mature mRNA, and whether the reading frame of dystrophin mature mRNA thereby can be corrected and dystrophin negative cells thus can be converted into positive ones, and to provide, on the basis of the results, a therapeutic agent.

As will be described later in greater detail, the present inventors pursued the study toward the above objectives. It was then demonstrated that an antisense oligonucleotide against dystrophin exon 19, when added to the culture medium of myoblasts of a DMD patient with a simple loss of exon 20, was incorporated into the cells and then into the nucleus, and led to the restoration of the reading frame, which, with entire loss of exon 19 and 20, now returned in-frame from the previous out-of-frame position, thus giving a dystrophin which was full length except for the deleted part encoded by exons 19 and 20. This result strongly suggest the possibility that, by administering an antisense oligonucleotide against exon 19 to a patient of DMD with a simple loss of exon 20, the very severe case of DMD can be converted to a relatively mild BMD case. The present invention is based on these findings.

SUMMARY OF THE INVENTION

Thus, the present invention provides use of an antisense oligonucleotide for the manufacture of a therapeutic pharmaceutical composition for Duchenne muscular dystrophy with entire loss of exon 20 in the production of dystrophin mature mRNA, wherein said antisense oligonucleotide consists of a 20 to 50-nucleotide sequence against exon 19 of the dystrophin pre-mRNA. Use of such an antisense oligonucleotide as an active principle for a therapeutic pharmaceutical composition makes it possible, for a type of Duchenne muscular dystrophy having an entire loss of exon 20, to shift the amino acids reading frame in its mRNA from abnormal out-of-frame position to in-frame one, and this then enables to convert the disease to a less severe Becker muscular dystrophy.

Therefore, in another aspect of the present invention, it provides a therapeutic pharmaceutical composition for Duchenne muscular dystrophy with entire loss of exon 20 in the production dystrophin mature mRNA, wherein said therapeutic pharmaceutical composition comprises, in a pharmaceutically acceptable injectable medium, an antisense oligonucleotide consisting of a 20 to 50-nucleotide sequence against exon 19 of the dystrophin pre-mRNA.

In still another aspect of the present invention, it provides a method of treatment of a human patient with Duchenne muscular dystrophy with entire loss of exon 20 in the production dystrophin mature mRNA comprising administering to said patient an therapeutically effective amount of an antisense oligonucleotide consisting of 20 to 50-nucleotide sequence against exon 19 of the dystrophin pre-mRNA in a pharmaceutically acceptable injectable medium.

DETAILED DESCRIPTION OF THE INVENTION

In the present specification, "nucleotide" not only means DNA and RNA in their usual sense but also includes their phosphorothioate analogues. Phosphorothioate DNA and phosphorothioate RNA, which can make base pairs as usual DNA and RNA, are more resistant to various decomposition enzymes and therefore are employed in the present invention with special advantage. The term "phosphorothioate analogue" herein is of a structure in which one or more phosphorodiester groups between nucleotides of DNA or RNA are replaced with phosphorothioate group.

A particularly preferred one of the antisense oligonucleotides is the antisense oligonucleotide against the nucleotide sequence set forth under SEQ ID NO:1 in the Sequence Listing, which is the exon recognition sequence of exon 19. Therefore, particularly preferably the present invention provides the above-mentioned use of an antisense oligonucleotide for the manufacture of a therapeutic pharmaceutical composition for Duchenne muscular dystrophy with entire loss of 20, wherein said antisense oligonucleotide comprises a nucleotide sequence complementary to the nucleotide sequence set forth under SEQ ID NO:1 in the Sequence Listing.

The antisense oligonucleotide may be an oligoDNA, a phosphorothioate oligoDNA, or a phosphorothioate oligoRNA.

A particularly preferable example of the antisense oligonucleotides is an oligoDNA, a phosphorothioate oligoDNA or a phosphorothioate oligoRNA any of which has a nucleotide sequence complementary to the nucleotide sequence set forth under SEQ ID NO:2 in the Sequence Listing.

Further, the antisense oligonucleotides may be prepared in the form of a therapeutic pharmaceutical composition containing one of them in a pharmaceutically acceptable injectable medium for Duchenne muscular dystrophy with entire loss of exon 20 in the production of dystrophin mature mRNA.

Therefore present invention further provides a therapeutic pharmaceutical composition for Duchenne muscular dystrophy with entire loss of exon 20 in the production of dystrophin mature mRNA, wherein said therapeutic pharmaceutical composition comprises, in a pharmaceutically acceptable injectable medium, an antisense oligonucleotide consisting of a 20 to 50-nucleotide sequence against exon 19 of the dystrophin pre-mRNA.

A particularly preferred one of the antisense oligonucleotides is an antisense oligonucleotide against the exon recognition sequence of exon 19 set forth under SEQ ID NO:1 in the Sequence Listing. Therefore the present invention further provides the above-mentioned therapeutic pharmaceutical composition for Duchenne muscular dystrophy wherein said antisense oligonucleotide comprises a nucleotide sequence complementary to the nucleotide sequence set forth under SEQ ID NO:1 in the Sequence Listing.

The antisense oligonucleotide may be an oligoDNA, a phosphorothioate oligoDNA, or a phosphorothioate oligoRNA.

A particularly preferable example of the antisense oligonucleotides is an oligoDNA, a phosphorothioate oligoDNA or a phosphorothioate oligoRNA any of which has a nucleotide sequence complementary to the nucleotide sequence set forth under SEQ ID NO:2 in the Sequence Listing.

The therapeutic pharmaceutical composition of the present invention preferably contains 0.05–5 $\mu$moles/ml of one of the antisense oligonucleotides, 0.02–10%w/v of at least one carbohydrate or polyalcohol, and 0.01–0.4%w/v of at least one pharmaceutically acceptable surfactant. A more preferred concentration range for the antisense oligonucleotide is 0.1–1 $\mu$moles/ml.

For the above carbohydrate, monosaccharide or disaccharides is preferred. Examples of the carbohydrates and polyalcohols include glucose, galactose, mannose, lactose, maltose, mannitol, and sorbitol. One or more of them may be employed alone or in combination.

Examples of preferred surfactants include polyoxyethylene sorbitan mono- to tri-ester, alkyl phenyl polyoxyethylene, sodium taurocholate, sodium cholate, and polyalcohol esters. A particularly preferred one of them is polyoxyethylene sorbitan mono- to tri-ester, and particularly preferred esters are oleate, laurate, stearate, and palmitate. One or more of them may be employed alone or in combination.

The therapeutic pharmaceutical composition of the present invention preferably further contains 0.03–0.09 M of at least one pharmaceutically acceptable neutral salt, for example, sodium chloride, potassium chloride and/or calcium chloride.

The therapeutic pharmaceutical composition of the present invention preferably may further contain 0.002–0.05 M of a pharmaceutically acceptable buffering agent. Examples of preferable buffering agents include sodium citrate, sodium glycinate, sodium phosphate, and tris (hydroxymethyl)aminomethane. One of more of these buffering agents may be employed alone or in combination.

The above therapeutic pharmaceutical compositions may be supplied in liquid forms. Considering, however, for cases in which they must be kept for a certain length of time, generally it is preferred that they are in a lyophilized form in order to stabilize the antisense oligonucleotide and thereby preventing its therapeutic effect from lowering. Such a composition can be used after prior-to-use reconstruction, i.e., into a liquid form to be injected, with a solvent (e.g., injectable distilled water). Therefore the therapeutic pharmaceutical compositions of the present invention include those in lyophilized form which are intended to be reconstructed prior to use with a solvent to make its ingredients fall within predetermined concentration ranges. For greater stability of such lyophilized compositions, albumin or amino acids such as glycine may be added.

EXAMPLES

The present invention will be described in further detail below with reference to a set of tests conducted.

1. Induction of Exon Skipping in Lymphoblastoid Cells Derived from a Patient.

As already mentioned above, it was confirmed that the antisense oligonucleotide designed by the present inventors efficiently induced skipping of exon 19 in the splicing reaction on the pre-mRNA transcribed from the dystrophin gene with normal structure. On the other hand, it is expected that the dystrophin pre-mRNA of a DMD patient with deleted exon 20 is abnormal in its secondary or tertiary structure since its gene structure is different from normal one. Thus, study was made to examine whether the above-mentioned 31-base antisense oligonucleotide would work in such a DMD patient. Briefly, as will be described in detail below, an EB virus-transformed lymphoblastoid cell lines were established from two DMD patients who lacked dystrophin exon 20. Using these cell lines it was confirmed that the antisense oligonucleotide was able to induce exon skipping.

(a) Establishment of Lymphoblastoid Cell Lines from DMD Patients

EB virus-transformed lymphoblastoid cell lines were established as follows from two DMD patients who lacked dystrophin exon 20: Two ml of whole blood taken from each of the patients was mixed with 2 ml of RPMI 1640 medium (supplemented with 10% FBS) and loaded onto 3 ml of Ficoll Paque (Pharmacia) and then subjected to density-gradient centrifugation. Then, the lymphocyte layer was selectively collected, washed twice with RPMI1640 medium (supplemented with 10% FBS), and suspended in 0.5 ml of RPMI1640 medium (supplemented with 10% FBS) to give a lymphocyte suspension. This suspension was mixed with a 0.5 ml EB virus solution which had been prepared beforehand, and the mixture was cultured at 37° C. for a week. A week later, the culture was washed with RPMI1640 medium (supplemented with 10% FBS) in order to remove the EB virus, and culture was continued with the same medium. According to the procedures, the lymphocytes from the patients were infected with EB virus and gave morphologically large, lymphoblastoid cells.

(b) Incorporation of an Antisense Oligonucleotide

The above obtained culture of lymphoblastoid cell lines were centrifuged to separate cellar component. The cells were cultured at 36° C. for 5 hours in a maintenance medium containing about 200 nM (200 pmole/ml) of an antisense oligoDNA consisting of a 31-nucleotides sequence complementary to the nucleotide sequence set forth under SEQ ID NO:2 in the Sequence Listing and 2% of fetal bovine serum (FBS). The medium then was replaced with the serum medium and culture was continued for additional 12 hours. After the culture, the cells were collected and the whole RNAs extracted in a conventional manner.

(c) Analysis of Dystrophin cDNA

Using thus obtained whole RNAs as templates, cDNA were synthesized in a conventional manner by reverse transcriptase with hexaoligonucleotides as random oligonucleotide primers. Using thus obtained cDNAs, a region covering dystrophin exon 18 through exon 21 was amplified by nested PCR. The first cycle of amplification was carried out using primers matched to exon 18 and exon 21. Using this amplification product as a template, the second PCR was carried out with primers designed to match to inner sites from those designed for the first primers. This amplification was done with the annealing temperature set at 60° C.

(d) Confirmation of Exon 19 Skipping

The amplification of the region covering from exon 18 through exon 21 of dystrophin cDNA performed without addition of the antisense oligonucleotide gave a clear band with 384 base pairs. Sequencing of this amplification in a conventional manner product confirmed that it consisted of exons 18, 19 and 21. This conformed to the result of genetic analysis done on the patient.

On the other hand, with regard to cDNA prepared from the cells which received the antisense oligoDNA, a smaller-sized amplification product was also obtained with restored amino acids reading frame since the fourth day of culture, along with an amplification product with the same size as one obtained from the cells without incorporation of the antisense oligoDNA. By the same method, the lymphoblastoid cells established from the case 2 also gave two types of bands. Sequencing of the smaller-sized amplification products revealed that exon 18 sequence was connected directly to that of exon 21, with both exons 19 and 20 deleted. This indicates that the treatment with the antisense oligonucleotide caused skipping of exon 19. On the other hand, lymphoblastoid cells established from a normal donor gave only a smaller-sized amplification product in which exon 19 only was skipped. Examination performed on the whole dystrophin cDNA by amplifying it in different 10 regions revealed no fragment suggesting abnormality in splicing.

(e) Discussion

The observed difference in the exon skipping inducing effect of antisense oligonucleotide between the normal subject and the DMD patient seemed to be attributable to a difference in the secondary or tertiary structure around exon 19 of the pre-mRNA. Efficiency of exon skipping induction was further determined for DMD patient by applying the antisense oligonucleotide at different concentrations. However, no condition was found under which all the transcript undergoes exon skipping as shown in the cells derived from the normal subject. In addition, this induction observed with the antisense oligonucleotide was not observed with a sense oligonucleotide of antisense oligonucleotides against other regions.

These results indicate that it is possible to correct the amino acids reading frame of dystrophin pre-mRNA by inducing an exon skipping through manipulation of splicing process of it. It was still unclear, however, whether the protein would be efficiently synthesized also in muscular cells with a mRNA whose reading frame was restored by means of such a modification to it.

2. Expression of Dystrophin-like Protein in Muscular Cells from DMD Patient

Then, examination was conducted on whether a dystrophin-like protein would be expressed in myoblasts from a DMD patient who lacked exon 20.

(a) Establishment of a Muscular Cell Line from DMD Patient

A specimen of muscular tissue was aseptically taken from a patient who lacked exon 20 in dystrophin gene, minced and trypsinized to give isolated cells. The cells were washed and then cultured in a growth medium (Ham-F10 supplemented with 20% FCS and 0.5% chicken embryo extract). For subcultivation, the muscular cells were cultured on cover slips placed in a culture dish. When the proportion of myoblasts reached about 80%, the medium was replaced with Fusion medium (DMEM supplemented with 2% HS) to induce differentiation into muscular cells.

(b) Incorporation of Antisense OligoDNA

On the fourth day of induction of differentiation, antisense oligoDNA (200 pmol) was introduced into the cells using LipofectAMINE (6 μl), and further cultured for 3, 7 and 10 days.

(c) Immunohistochemical Staining of Dystrophin

After respective incubations, the cells were subjected to immunohistochemical staining using an antibody against the C-terminus of dystrophin. As a result, it was found that dystrophin staining turned positive in the cells in which no dystrophin staining had initially been detected. Dystrophin positive cells were found in any of the culture. In addition, staining with an antibody against the N-terminal region of dystrophin also gave a similar result to that obtained with the C-terminal staining, thus confirming that the produced dystrophin extended from the N-terminus to the C-terminus.

While dystrophin staining was thus positive in the myoblasts which received the antisense oligoDNA, no dystrophin staining was noted in myoblasts treated likewise but without addition of the antisense oligoDNA.

(d) Analysis of Dystrophin cDNA

Then, RNA was extracted by a conventional method from the above myoblasts cultured with the antisense oligoDNA. After the synthesis of cDNA from the RNA thus obtained, a region covering dystrophin exons 18–21 was amplified as described above with regard to the RNA from lymphoblastoid cells.

The amplification product was then sequenced by a conventional method. As a result, it was found that the amplification product was obtained whose amino acids reading frame had been turned in-frame by a direct connection of the exon 18 sequence to that of exon 21 since the fourth day of culture.

Then the cDNA prepared from the myoblasts cultured with the antisense oligoDNA was amplified by PCR in 10 different portions which altogether covered the whole cDNA. The amplified fragments were electrophoreses to determine their sizes by a conventional method. As a result, no fragment suggesting abnormal splicing was noted except for the skipping of exons 19 and 20. These results indicate that the obtained dystrophin mature mRNA was a reading frame-restored, full length mRNA except for the entire loss of exons 19 and 20.

3. Transfer of Antisense OligoDNA into the Nucleus

Then, in order to obtain supportive evidence that the antisense oligoDNA had actually transferred into the nucleus and worked in it, a fluorescence-labelled antisense oligoDNA was used to observe its transfer into the nucleus.

The antisense oligoDNA used above was labelled with FITC (fluorescein isothiocyanate) by a conventional method, and its transfer into the nucleus was examined. Briefly, muscular cells from a DMD patient was cultured in a growth medium (Ham-F10 supplemented with 20% FCS and 0.5% chicken embryo extract). The culture was performed on cover slips placed in a culture dish. When the cells became semiconfluent, the medium was replaced with Fusion medium (DMEM supplemented with 2% HS) to induce differentiation into the muscular cells. On the fourth day of induction of differentiation, antisense oligoDNA (200 pmol) was introduced into the cells using LipofectAMINE (6 μl), and 1, 2, 3, 7 and 10 days later, localization of FITC was assessed.

As a result, fluorescence signal was detected in the nucleus. This supports that the antisense oligoDNA actually transferred into the nucleus and there caused skipping of exon 19 splicing.

As demonstrated by the above experimental results, the present invention can allow synthesis of a protein corresponding to dystrophin to take place in the myoblasts of a DMD patient by restoring the amino acids reading frame into in-frame position. This indicate a possibility that patients suffering from the very severe, so far incurable disease of DMD, in particular that with simple loss of exon 20, can be converted to milder BMD patients.

In the present invention, antisense oligonucleotide may be oligoDNA, phosphorothioate oligoRNA or phosphorothioate oligoDNA. Phosphorothioate nucleotides referred to herein are nucleotides in which the oxygen atom in the phosphate group is replaced with a sulfur atom. They are nucleotide analogues more resistant to various nucleotide decomposition enzymes and therefore widely used in the field of genetic engineering for site specific substitution of genes or the like, and their method of production, properties and a variety of application are well known to those skilled in the art. Antisense phosphorothioate oligoDNA is more stable than antisense oligoDNA and therefore provide a particular benefit when used in the present invention.

Administration of an antisense oligonucleotide of the present invention to a DMD patient with a simple loss of exon 20 can be made as follows, for example: Antisense oligoDNA, antisense phosphorothioate oligoDNA or antisense phosphorothioate oligoRNA complementary to the nucleotide sequence set forth under SEQ ID NO:2 in the Sequence Listing produced by a conventional method well known to those skilled in the art is sterilized by a conventional method and formed into e.g., a 1200 μg/ml injectable solution. The solution is then intravenously administered to a patient, for example by dropwise infusion of a parenteral fluid, at a dose of for example 20 mg of the antisense oligonucleotide per kg body weight. Its administration is made four time at two-week intervals, for example. Later administration is repeated according to the needs while monitoring the expression of dystrophin protein in the muscle tissue biopsy sample, serum creatine kinase levels, and therapeutic effect assessed on the basis of the clinical symptoms. As far as it takes effect and no apparent side effect is observed, the therapy is generally-continued over the patient's life.

The present invention is described in further detain with reference to some representative examples blow. It is not intended, however, that the scope of the present invention be restricted to the examples.

Example 1

Preparation of Antisense OligoDNA, Phosphorothioate OligoDNA, Phosphorothioate OligoRNA DNA, phosphorothioate oligoDNA, phosphorothioate oligoRNA having a nucleotide sequence complementary to the nucleotide sequence set forth under SEQ ID NO:2 in the Sequence Listing is produced using a commercially available DNA synthesizer such as Applied Biosystems Model 1380B, and according to the method described in Zon et al., [Oligonucleotides and Analogues: A Practical Approach, F. Eckstein, Ed., p.87–108, Oxford University Press, Oxford, England; U.S. Pat. No. 5,151,510].

Composition Example 1

According to the following formula, necessary amount of respective base materials are admixed to dissolve. The antisense oligonucleotide is then dissolved in the solution, the solution is made to volume and filtered through a membrane filter with a pore size of 0.22 μm to obtain a composition for intravenous administration.

| | |
|---|---|
| Antisense oligonucleotide (*1) | 500 mg |
| Sodium chloride | 8.6 g |
| Potassium chloride | 0.3 g |
| Calcium chloride | 0.33 g |
| Injectable distilled water | to 1000 ml |

*1: phosphorothioate oligoDNA having a nucleotide sequence complementary to the nucleotide sequence set forth under SEQ ID NO:2 in the Sequence Listing

Composition Example 2

According to the following formula, necessary amount of respective base materials are admixed to dissolve. The antisense oligonucleotide is then dissolved in the solution, the solution is made to volume and filtered through a filter with a pore size of 15 nm (PLANOVE 15: Asahi Chemical Industry Co., Ltd.) to obtain a composition for intravenous administration.

| | |
|---|---|
| Antisense oligonucleotide (*2) | 100 mg |
| Sodium chloride | 8.3 g |
| Potassium chloride | 0.3 g |
| Calcium chloride | 0.33 g |
| Sodium hydrogen phosphate.12H$_2$O | 1.8 g |
| 1 N hydrochloric acid | q.s. (pH 7.4) |
| Injectable distilled water | to 1000 ml |

*2: phosphorothioate oligoDNA having a nucleotide sequence complementary to the nucleotide sequence set forth under SEQ ID NO:2 in the Sequence Listing

Composition Example 3

According to the following formula, necessary amount of respective base materials are admixed to dissolve. The antisense oligonucleotide is then dissolved in the solution, the solution is made to volume and filtered through a filter with a pore size of 35 nm (PLANOVE 35: Asahi Chemical Industry Co., Ltd.) to obtain a composition for intravenous administration.

| | |
|---|---|
| Antisense oligonucleotide (*3) | 100 mg |
| Sodium chloride | 8.3 g |
| Potassium chloride | 0.3 g |
| Calcium chloride | 0.33 g |
| Sodium hydrogen phosphate.12H$_2$O | 1.8 g |
| 1 N hydrochloric acid | q.s. (pH 7.4) |
| Injectable distilled water | to 1000 ml |

*3: phosphorothioate oligoDNA having a nucleotide sequence complementary to the nucleotide sequence set forth under SEQ ID NO:2 in the Sequence Listing

What is claimed is:

1. A method of manufacturing a composition, the method comprising:
   forming an antisense oligonucleotide consisting of a nucleotide sequence fully complementary to the sequence represented by SEQ ID NO: 1;
   dissolving the antisense oligonucleotide in a pharmaceutically acceptable injectable medium to form a solution; and
   sterilizing the solution to form a composition for intravenous administration.

2. The method of claim 1, wherein the antisense oligonucleotide comprises oligoDNA, phosphorothioate oligoDNA, or phosphorothioate oligoRNA.

3. A method of manufacturing a composition comprising:
   forming an antisense oligonucleotide consisting of a nucleotide sequence fully complementary to the sequence represented by SEQ ID NO: 2;
   dissolving the antisense oligonucleotide in a pharmaceutically acceptable injectable medium to form a solution; and
   sterilizing the solution to form a composition for intravenous administration.

4. The method of claim 3, wherein the antisense oligonucleotide comprises oligoDNA, phosphorothioate oligoDNA, or phosphorothioate oligoRNA.

5. A composition comprising:
   in a pharmaceutically acceptable injectable medium,
   an antisense oligonucleotide consisting of a nucleotide sequence fully complementary to the nucleotide sequence represented by SEQ ID NO: 1 or SEQ ID NO: 2.

6. The composition of claim 5, wherein the antisense oligonucleotide comprises oligoDNA, phosphorothioate oligoDNA, or phosphorothioate oligoRNA.

7. The composition of claim 5, comprising 0.05–5 μmol/mL of the oligonucleotide, 0.02–10 w/v % of at least one carbohydrate or polyalcohol, and 0.0 1–0.4 w/v % of at least one pharmaceutically acceptable surfactant.

8. The composition of claim 7, wherein the at least one of carbohydrate or polyalcohol comprises carbohydrate comprising monosaccharides or disaccharides.

9. The composition of claim 7, wherein the at least one of carbohydrate or polyalcohol comprises glucose, galactose, mannose, lactose, maltose, mannitol, or sorbitol.

10. The composition of claim 7, wherein the pharmaceutically acceptable surfactant comprises polyoxyethylene sorbitan mono- to tri-ester, alkyl phenyl polyoxyethylene, sodium taurocholate, sodium cholate, or polyalcohol ester.

11. The composition of claim 7, wherein the pharmaceutically acceptable surfactant comprises polyoxyethylene sorbitan ester comprising oleate, laurate, stearate, or palmitate.

12. The composition of claim 5, further comprising 0.03–0.09 M of at least one pharmaceutically neutral salt.

13. The composition of claim 12, wherein the neutral salt is selected from at least one of sodium chloride, potassium chloride, or calcium chloride.

14. The composition of claim 5, further comprising 0.002–0.05 M of a pharmaceutically acceptable buffering agent.

15. The composition of claim 14, wherein the buffering agent is selected from at least one of sodium citrate, sodium glycinate, sodium phosphate, or tris(hydroxymethyl) aminomethane.

16. The composition of claim 5, wherein the composition is in lyophilized form.

* * * * *